(12) United States Patent
Ballerstadt et al.

(10) Patent No.: US 7,226,414 B2
(45) Date of Patent: Jun. 5, 2007

(54) METHOD AND APPARATUS FOR ANALYTE SENSING

(75) Inventors: Ralph Ballerstadt, Houston, TX (US); Roger McNichols, Pearland, TX (US); Ashok Gowda, Houston, TX (US)

(73) Assignee: BioTex, Inc., Houston, TX (US)

( * ) Notice: Subject to any disclaimer, the term of this patent is extended or adjusted under 35 U.S.C. 154(b) by 637 days.

(21) Appl. No.: 10/678,814

(22) Filed: Oct. 3, 2003

(65) Prior Publication Data

US 2004/0072358 A1    Apr. 15, 2004

Related U.S. Application Data

(60) Provisional application No. 60/417,398, filed on Oct. 9, 2002.

(51) Int. Cl.
*A61B 5/00* (2006.01)

(52) U.S. Cl. ............... 600/365; 600/347; 204/400; 42/68.1

(58) Field of Classification Search ............... None
See application file for complete search history.

(56) References Cited

U.S. PATENT DOCUMENTS

| | | | |
|---|---|---|---|
| 4,005,699 A * | 2/1977 | Bucalo | .......... 600/12 |
| 4,041,932 A | 8/1977 | Fostick | |
| 4,071,020 A | 1/1978 | Pugliese | |
| 4,261,968 A | 4/1981 | Ullman et al. | |
| 4,330,299 A | 5/1982 | Cerami | |
| 4,344,438 A | 8/1982 | Schultz | |
| 4,401,122 A | 8/1983 | Clark, Jr. | |
| 4,419,383 A * | 12/1983 | Lee | .......... 427/550 |
| 4,450,104 A | 5/1984 | Jordan | |
| 4,868,103 A | 9/1989 | Stavrianopoulos et al. | |
| 4,981,779 A | 1/1991 | Wagner | |
| 5,001,051 A | 3/1991 | Miller et al. | |
| 5,028,787 A | 7/1991 | Rosenthal et al. | |

(Continued)

OTHER PUBLICATIONS

"Fiber-Optic Biosensors Based on Fluorescence Energy Transfer", Meadows et al., Talanta, vol. 35, No. 2, pp. 145-150, 1988.

(Continued)

*Primary Examiner*—Charles A. Marmor, II
*Assistant Examiner*—Patricia Mallari
(74) *Attorney, Agent, or Firm*—Neil A. Steinberg

(57) ABSTRACT

In one aspect, the present invention is directed to a glucose sensing device for implantation within subcutaneous tissue of an animal body. In one embodiment, the glucose sensing device includes a first chamber containing first magnetic particles and a hydrocolloid solution (for example, ConA-dextran hydrocolloid) wherein the first magnetic particles are dispersed in the hydrocolloid solution. In operation, glucose within the animal may enter and exit the first chamber and the hydrocolloid solution changes in response to the presence or concentration of glucose within the first chamber. The sensing device also includes a reference chamber containing second magnetic particles and a reference solution wherein the second magnetic particles are dispersed in the reference solution. The reference solution (for example, oil or alcohol compounds) includes a known or fixed viscosity. The reference solution may also be a hydrocolloid solution (for example, ConA-dextran hydrocolloid). The first and/or second magnetic particles may include amine-terminated particles, at least one rare earth element (for example, neodymium or samarium), and/or a ferromagnetic material.

66 Claims, 4 Drawing Sheets

U.S. PATENT DOCUMENTS

| | | | |
|---|---|---|---|
| 5,101,814 | A | 4/1992 | Palti |
| 5,143,066 | A | 9/1992 | Komives et al. |
| 5,244,636 | A | 9/1993 | Walt et al. |
| 5,320,814 | A | 6/1994 | Walt et al. |
| 5,326,531 | A | 7/1994 | Hahn et al. |
| 5,341,805 | A | 8/1994 | Stavridi et al. |
| 5,342,789 | A | 8/1994 | Chick et al. |
| 5,460,971 | A | 10/1995 | Gottlieb |
| 5,654,419 | A | 8/1997 | Mathies et al. |
| 5,780,247 | A | 7/1998 | Satomura et al. |
| 5,814,449 | A | 9/1998 | Schultz et al. |
| 6,040,194 | A | 3/2000 | Chick et al. |
| 6,110,660 | A * | 8/2000 | Kriz et al. ............ 435/4 |
| 6,210,326 | B1 | 4/2001 | Ehwald |
| 6,267,002 | B1 | 7/2001 | Ehwald et al. |
| 6,383,767 | B1 | 5/2002 | Polak |
| 6,477,891 | B2 | 11/2002 | Ehwald et al. |
| 6,485,703 | B1 | 11/2002 | Cote et al. |
| 6,579,498 | B1 * | 6/2003 | Eglise ............ 422/82.05 |
| 6,694,158 | B2 | 2/2004 | Polak |
| 6,846,638 | B2 | 1/2005 | Shipwash |
| 2001/0035047 | A1 | 11/2001 | Ehwald et al. |
| 2001/0045122 | A1 | 11/2001 | Ehwald et al. |
| 2002/0087145 | A1 | 7/2002 | Ehwald et al. |
| 2003/0049625 | A1 | 3/2003 | Heyduk |
| 2003/0054560 | A1 | 3/2003 | Ehwald et al. |
| 2003/0059811 | A1 | 3/2003 | Djaballah et al. |
| 2003/0228682 | A1 | 12/2003 | Lakowicz et al. |

OTHER PUBLICATIONS

"Chemiluminscent and Fluorescent Probes for DNA Hybridization Systems", Heller et al., DNA Hybridization Systems, pp. 245-257 (1985).

"Detection of Nucleic Acid Hybridization by Nonradiative Fluorescence Resonance Energy Transfer", Cardullo et al., Proc. Natl. Acad. Sci. U.S.A., vol. 85, pp. 8790-8794, Dec. 1988.

"Affinity Sensor: A New Technique for Developing Implantable Sensors for Glucose and Other Metabolites", Schultz et al., Diabetes Care, vol. 5, No. 3, pp. 245-253 (1982).

"A Fluorescence Affinity Hollow Fiber Sensor for Continuous Transdermal Glucose Monitoring", Ballerstadt et al., Analytical Chemistry, Vo. 72, No. 17, pp. 4182-4197 (2000).

* cited by examiner

METHOD AND APPARATUS FOR ANALYTE SENSING

CROSS-REFERENCE TO RELATED APPLICATIONS

This application claims priority to: U.S. Provisional Application Ser. No. 60/417,398, entitled "Method and Apparatus for Analyte Sensing", filed Oct. 9, 2002. The contents of this provisional application are incorporated by reference herein in its entirety.

BACKGROUND OF THE INVENTION

1. Field of Invention

This invention is directed to a method and an apparatus to facilitate minimally invasive measurement, sampling and/or sensing of analytes, for example, glucose, in a fluid, matrix or animal body.

2. Description of the Related Art

Glucose sensing is an important diagnostic tool in therapy and research of Diabetes mellitus. Diabetes is a chronic systemic disease characterized by disorders in the metabolism of insulin, carbohydrate, fat, and protein as well as in the structure and function of blood vessels. Currently, diabetes is a leading cause of death in the United States, and more than sixteen million Americans are believed to have this disease. Intensive management of blood sugars through frequent monitoring is effective to prevent, or at least manage, the progression of diabetic complications such as kidney failure, heart disease, gangrene, and blindness.

Maintaining blood glucose levels near normal levels is typically achieved by frequently monitoring the blood glucose. Currently the most common method of sensing is a colorimetric/electro-enzymatic approach, which is invasive. In short, the colorimetric/electro-enzymatic approach requires blood to be drawn and tested. This often requires a finger stick to draw blood each time a reading is needed. In sum, this approach is typically time-consuming and quite painful.

Minimally invasive approaches based on needle-type enzyme sensors (e.g. glucose oxidase) have been investigated as a less painful method of estimating blood glucose concentrations. Such approaches, however, have well-known limitations of measurement of glucose in interstitial fluid. For example, such approaches often suffer from a limitation on the accuracy and stability of the glucose measurement. In this regard, the chemical instability and/or external biocompatibility issues tend to adversely affect the signal sensitivity and stability of the sensor over time. As such, there exists a need for a minimally invasive approach that overcomes one, some or all of the well-known limitations.

SUMMARY OF THE INVENTION

There are many inventions described and illustrated herein. In one aspect, the present invention relates to a system, sensor and method for minimally invasively sensing the glucose level in a fluid, matrix or animal body. In one embodiment, the sensor device utilizes a hydrocolloid (for example, glucose-binding molecules and macromolecules, such as glucose-terminated or mannose-terminated), which is in communication with fluid under investigation, for example a fluid of an animal body.

In one embodiment, the concentration of glucose in the fluid under investigation is determined, detected and/or measured by applying an external magnetic field to the sensor device and measuring the speed of migration of magnetic particles (e.g., paramagnetic, superparamagnetic, and/or ferromagnetic particles) dispersed within the hydrocolloid solution/medium. The concentration of glucose in the fluid may be determined, calculated, measured or sensed from the speed or velocity of the movement or migration of magnetic particles within the solution. In this regard, the viscosity of the hydrocolloid is dependent on, or a function of the concentration of glucose in the fluid.

Briefly, by way of background, a specific binding reaction of a multivalent receptor molecule, like Concanavalin A, in a highly concentrated dispersion of high-molecular weight dextran may cause a significant increase in fluid viscosity due to intermolecular affinity cross-linking (see FIG. 1). In the absence of glucose, the affinity binding of dextran by ConA tends to require a higher force to move fluid layers in the dispersion, resulting in a highly viscous dispersion. However, in the presence of glucose, dextran may be competitively displaced from the binding sites of ConA, tending thereby to decrease or minimize the force required to move fluid layers along each other, and, hence, reducing the dispersion viscosity. This reduction of viscosity due to the action of glucose may surpass the viscosity contribution of glucose to the total viscosity by several orders of magnitude.

The sensor device according to one embodiment of the present invention may be implanted beneath the skin of, or in convenient and/or readily accessible location in an animal body where the sensor is in contact with body fluids containing glucose. A magnetic field may be externally applied to the body, and using instrumentation, the level of glucose in the interstitial fluid or other surrounding body fluid may be measured, quantified, sensed or detected. In this regard, the level of glucose may be determined by measuring or detecting the viscosity of the medium within the sensor.

In one embodiment of this aspect of the invention, the mechanism or technique measures, senses, detects or quantifies the viscosity of the sensing medium without disrupting the skin barrier, or with minimal or little disruption of the skin barrier of an animal body. In this regard, an external magnetic field may be applied above the sensor in order to cause or initiate movement of the paramagnetic or superparamagnetic particles in or through the sensing media. As the paramagnetic or superparamagnetic particles move in or through the sensing media, the sensor or external instrumentation may detect or sense that movement and detect or sense the position of the particles within the sensing media relative to the sensor body chambers.

The sensor or external instrumentation may also record the time required or taken for the particles to migrate a predetermined or known distance within the sensor. The sensor or external instrumentation may determine, measure or calculate the velocity of the magnetic particles in or through the sensing media. Using information which is representative of the velocity of the magnetic particles, the sensor or external instrumentation may determine, measure or calculate the viscosity of the medium in the chambers (for example, the glucose chamber). The viscosity of the medium in the glucose sensing chamber may then be related or correlated to a glucose concentration in the chamber. That is, in one embodiment, the concentration of glucose in the fluid may be determined, derived or calculated from the viscosity information. Thus, in one aspect, the present invention is directed toward a medium whose viscosity is determined, dependent and/or controlled, at least in part, by the concentration of glucose in said medium.

In one embodiment, the sensor may consist of a two-chambered sensor body having a reference chamber comprised of a material impermeable to glucose (for example, a glass capillary tube). In this regard, the reference chamber includes an impermeable membrane.

The glucose chamber may be comprised of a material which retains the sensing medium and, in addition, allows concentration driven transport of glucose into and out of the chamber (for example, a hollow micro dialysis fiber). In this regard, the glucose chamber includes a semipermeable membrane.

The sensing media may include micron-sized paramagnetic, superparamagnetic, and/or ferromagnetic particles that are capable of moving through the media (i.e., the sensing and reference media). The paramagnetic, superparamagnetic, and/or ferromagnetic particles, in operation, may be manipulated or moved by an externally applied magnetic field, for example, the field from a magnet applied to the skin above the implanted sensor.

The sensor body and/or magnetic particles, according to one embodiment, may include an identification or signature that permits the position of the particles to be determined or measured in the sensing medium relative to the sensor body. The identification techniques may include fluorescent or dye labels attached or adjacent to the magnetic particles.

The identification techniques may include electronic proximity and/or optical position sensors that are integrated within the sensor body to detect or sense the relative location or movement of the magnetic particles within the chambers of the sensor. The sensor may also consist of an in-dwelling needle-type body where the above features are coupled directly to outside instrumentation rather than sensing through the skin barrier, via, for example, optical, inductive, or capacitive coupling.

In another aspect, the present invention is a means, mechanism and method to integrate a viscosity sensing means into the sensor body.

In yet another aspect, the present invention is directed toward providing a self-contained micro-dialysis viscometer sensor that is based, at least partially, on the sensor device described above (and to be described below).

In another aspect, the present invention is a reference sensor device, including a reference sensing medium therein, to calibrate the sensor device by deriving, determining and/or calculating calibration parameters for subsequent viscosity measurements. In this regard, the sensor device, after such calibration, may be employed to determine, quantify, detect and/or measure the concentration of glucose in a fluid, for example, the interstitial fluid or other surrounding fluid in an animal body. The concentration of glucose in the fluid may be determined, derived or calculated from the viscosity information. Thus, in one aspect, the present invention is a method for determining the viscosity of the glucose sensing medium based on calibrating measurements obtained from the reference sensing medium having known viscosity.

Again, there are many inventions described and illustrated herein. This Summary is not exhaustive of the scope of the present invention. Moreover, this Summary is not intended to be limiting of the invention and should not be interpreted in that manner. While certain embodiments, features, attributes and advantages of the inventions have been described here, it should be understood that many others, as well as different and/or similar embodiments, features, attributes and/or advantages of the present inventions, which are apparent from the description, illustrations and claims—all of which follow.

BRIEF DESCRIPTION OF THE DRAWINGS

In the course of the description to follow, reference will be made to the attached drawings. These drawings show different aspects of the present invention and, where appropriate, reference numerals illustrating like structures, components, circuitry and/or elements in different figures are labeled similarly. It is understood that various combinations of the structures, components, circuitry, fluids, techniques and/or elements other than those specifically illustrated are contemplated and within the scope of the present invention.

DETAILED DESCRIPTION

Figure 1:
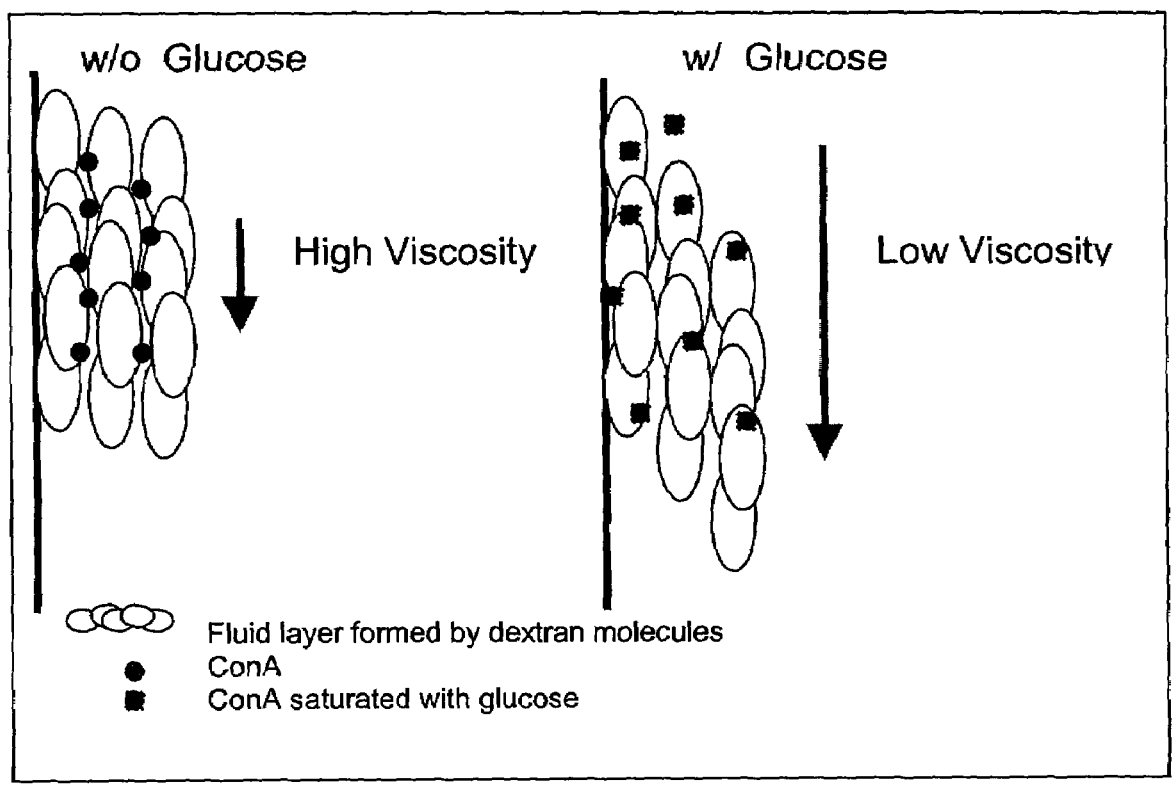
FIG. 1 is a schematic representation of the molecular phenomenon of glucose-induced viscosity changes in a ConA/dextran dispersion. In the absence of glucose, tetra- and bi-valent ConA molecules may bind together various dextran molecules. This may increase the viscosity of the solution by increasing the force to move fluid layers (simplified by dextran layers) along each other (left). However, in the presence of glucose, ConA dissociates from dextran by the competitive action of glucose, which may result in a lower viscosity (right)
Figure 2:
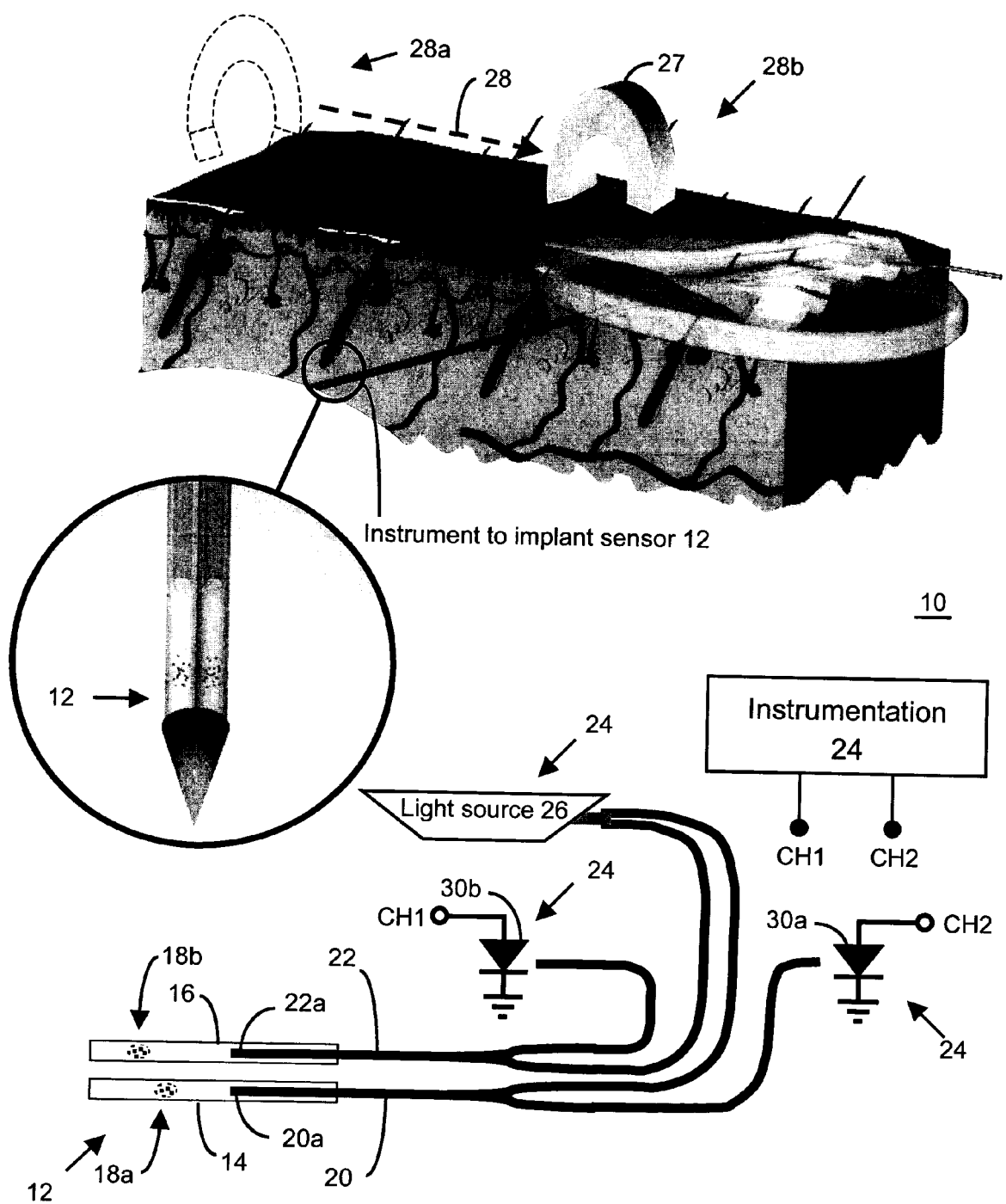
FIG. 2 is a schematic representation of a system, device and technique according to one embodiment of the present invention.

With reference to FIG. 2, the glucose sensing system 10, according to one embodiment of the present invention, includes sensor 12 having glucose chamber 14 and reference chamber 16. The sensor 12, in one embodiment, is implanted into or beneath the skin barrier of an animal body using a small needle-type instrument. In this regard, sensor 12 may be disposed within the subcutaneous tissue when the small needle-type housing is introduced through the skin. Thereafter, the sensor 12 may be affixed in place within subcutaneous tissue after the small needle-type housing is withdrawn.

In one embodiment, glucose and reference chambers 14 and 16, respectively, include magnetic (e.g., paramagnetic, superparamagnetic, and/or ferromagnetic) particles 18a and 18b, respectively, that are dispersed in a Concanavalin A ("ConA")—dextran hydrocolloid (for example, 5% dextran ($M_w$ 2000 kDa) and 1% ConA (volume of 0.5 μl)). In one embodiment the magnetic particles 18a and 18b are may be a particle or particles which may be made or caused to move under the influence of a magnetic field or magnetomotive force, for example, amine-terminated particles having mean diameter of about 1 μm (Bangs Laboratories, Inc., Part No. MC05N). As such, the magnetic particles may include rare earth elements like neodymium and samarium and compounds like neodymium-iron-boron and samarium-cobalt, and ferromagnetic materials including iron, permalloy, superpermalloy, cobalt, nickel, steel, and alnico. Indeed, any and all particles that may be caused to move under the influence of a magnetic field or magnetomotive force, whether now known or later developed, are intended to be within the scope of the present invention.

When implanted, the glucose in the tissue surrounding the sensor 12 may enter glucose chamber 14 and may interact with the medium in the chamber, including the concanavalin A ("ConA")—dextran hydrocolloid to effect, alter, modify and/or change the viscosity of the medium within chamber 14. The resultant viscosity, in turn, may determine, effect, alter, modify or change the rate at which the magnetic particles 18a move, travel or migrate through the medium of glucose chamber 14 under the influence of an applied magnetic field.

In one embodiment, glucose chamber 14 includes a semi-permeable membrane. In this regard, glucose chamber 14 may be comprised of a material which retains the sensing medium and, in addition, allows concentration driven transport of glucose into and out of the chamber (for example, a hollow micro dialysis fiber). In one embodiment, glucose chamber 14 may be comprised of regenerated cellulose, polyurethane, polysulfone, and/or other material that is capable of unrestricted (or substantially unrestricted) glucose in and efflux.

The reference chamber 16 may be disposed adjacent to, or in the vicinity of glucose chamber 14. The reference chamber 16 also includes a mixture of paramagnetic, superparamagnetic, and/or ferromagnetic particles 18b and a ConA/dextran hydrocolloid. The reference chamber 16 prohibits, limits or controls the glucose concentration in the paramagnetic or superparamagnetic particles and a ConA/dextran hydrocolloid mixture (i.e., collectively called the reference medium). In this regard, the reference chamber 16 may prohibit, limit or control the fluidic communication between the reference medium and the external fluid (i.e., the fluid in the tissue surrounding reference chamber 16 and/or sensor 12). As such, reference chamber 16 includes a fixed, predetermined, known or controlled concentration of glucose (for example, 100 mg/dL), and hence a known viscosity.

Because, the glucose concentration in reference chamber 16 remains constant, fixed, predetermined and/or known, and hence the viscosity of the medium in reference chamber 16 also remains constant, fixed, predetermined and/or known, the "travel" time of magnetic particles 18b within the chamber, therefore depends on, or is a function of the strength of an applied magnetic field. In one embodiment, reference chamber 16 includes an impermeable membrane. In this regard, reference chamber 16 is comprised of a material impermeable to glucose (for example, a glass capillary tube or plastic tubing (for example, Teflon, polyester PVC, acrylic, or polycarbonate)).

It should be noted that reference chamber 16 may contain fluid that does not include a glucose/ConA/dextran hydrocolloid. In this regard, reference chamber 16 may contain or be comprised of any fluid of known or constant viscosity. For example, oils, alcohols, aqueous solutions, or other compounds with known fixed viscosity may be employed as the fluid medium in reference chamber 16.

With continued reference to FIG. 2, at a proximal end of each chamber 14 and 16, optical fibers 20 and 22, respectively, are positioned. As such, light may be applied to optical fibers 20 and 22 (via light source 26) and enter chambers 14 and 16 via distal ends 20a and 22a. Moreover, light may be received from chambers 14 and 16 by optical fibers 20 and 22, respectively, at distal ends 20a and 22a, respectively. The proximal end of optical fibers 20 and 22 may be coupled to instrumentation 24 for measurement of reflectance, absorption, and/or fluorescence of magnetic particles 18a and 18b, or the chemistry attached thereto.

Light source 26 may be any suitable one or combination of laser, lamp, bulb such as incandescent or arc, light emitting diode (LED), electrical element or other mechanism for producing optical radiation. Further, light source 26 may include one or more optical elements such as filters, monochromaters, crystals, or other mechanism designed to condition optical radiation for use in instrumentation 24.

In operation, an external magnet 27 (for example, a NdFeBLa permanent type magnet) is disposed over sensor 12. The magnetic particles 18a and 18b in each chamber 14 and 16, respectively, are attracted to the magnetic field produced or provided by magnet 27. The magnet 27 is moved from a first position 28a to a second position 28b along dashed line 28. That is, magnet 27 is started at or near a first end of the chambers 14 and 16, and moved at a rate that is sufficient to ensure that a sufficient amount of magnetic particles 18a and 18b have moved, traveled or migrated to a second end of chambers 14 and 16.

Thus, magnetic particles 18a and 18b move, travel or migrate in response to magnet 27 moving from first position 28a to second position 28b. The instrumentation 24 coupled to optical fibers 20 and 22 is used to sense, monitor, measure and/or determine the proximity of magnetic particles 18a and 18b.

In one embodiment, instrumentation 24 measures or determines information representative of the reflectance, absorption, and/or fluorescence of the media in chambers 14 and 16. In this regard, instrumentation 24 may include a light source 26 (for example, a 633 nm HeNe laser), coupled to the inputs of optical fibers 20 and 22, and photo detectors 30a and 30b, each coupled to a respective output of optical fibers 20 and 22. As such, in operation, light source 26 transmits light to chambers 14 and 16 via optical fibers 20 and 22. The media in chambers 20 and 22 reflects a certain portion of the light to photo detectors 30a and 30b, via optical fibers 20 and 22, respectively. In response, photo detectors 30a and 30b sense, measure and/or record the intensity and/or presence of reflected light.

As magnet 27 moves from first position 28a to second position 28b, the reflectance of the media in chambers 14 and 16 changes. In this regard, the reflectance increases as magnetic particles 18a and 18b move towards distal ends 20a and 22a of optical fibers 20 and 22. The reflectance may be a maximum when particles 18a and 18b are in contact or substantially in contact with the face of the optical fiber. The instrumentation 24 measures the migration of particles effected by movement of magnet 27 and correlates that migration to the changes in the reflectance, as measured by photo detectors 30a and 30b.

Thus, by measuring the time interval of movement of magnet 27 relative to changes in reflectance of the media in chambers 14 and 16, the velocity of particles 18a and 18b may be determined, measured and/or calculated. In one embodiment, instrumentation 24 employs the time required for photo detectors 30a and 30b to record a maximum signal subsequent to the movement of magnet 27 from first position 28a to second position 28b.

Using that information, instrumentation 24 may determine or calculate the velocity of particles 18a and 18b in glucose chamber 14 and reference chamber 16, respectively. The migration time of the particles 18b in reference chamber 16 may be used to determine the strength of the applied magnetic field since the viscosity of medium in reference chamber 16 is known, predetermined, controlled and/or fixed. The instrumentation 24 uses the strength of the magnetic field and the migration time of the particles in glucose chamber 14 to determine, calculate or sense the viscosity of the medium in glucose chamber 14. As mentioned above, the viscosity of the medium may be a function of, or dependent on concentration of glucose in the medium.

Other techniques and devices may be employed to detect the location of the paramagnetic, superparamagnetic, and/or ferromagnetic particles. For example, in addition or in substitution of measuring, sensing or determining reflected light, as described above, system 10 may use an absorption technique. In this regard, instrumentation 24 may detect, sense, determine and/or measure a particular wavelength(s) of light which is/are strongly absorbed by particles 18*a* and 18*b*. The proximity of particles 18*a* and 18*b* to distal ends 20*a* and 22*a* of optical fibers 20 and 22, respectively, may result in an attenuation of the reflected signal at one, some, certain or all wavelengths of the applied light. In one embodiment, the wavelength attenuation may be enhanced by incorporating a non-motile (that is, non-magnetic) scattering agent such as $TiO_2$ in the media in glucose chamber 14 and/or reference chamber 16.

In another embodiment, system 10 may employ a fluorescence detection technique to measure, sense and/or determine the proximity of magnetic (i.e., paramagnetic, superparamagnetic, and/or ferromagnetic) particles 18*a* and 18*b*. In this regard, fluorescent dye molecules may be attached (for example, chemically) to magnetic particles 18*a* and/or 18*b*. In this way, a fluorescence excitation wavelength may be transmitted into the medium within chambers 14 and 16 by optical fibers 20 and 22, respectively. In response, fluorescent emission from tagged particles is measured by instrumentation 24. The intensity of such fluorescence emission may increase as the particles approach optical fiber 20 and/or 22.

In yet another embodiment, system 10 may employ techniques based on changes in electrical impedance, inductance and/or capacitance at one or more locations along chambers 14 and 16. In this regard, instrumentation 24, via wires or electrical or electromagnetic coupling, may detect the changes in the impedance, inductance and/or capacitance at predetermined locations in order to determine the velocity of particles 18*a* and 18*b*. The changes in the impedance, inductance and/or capacitance may allow instrumentation 24 to measure, detect, sense or calculate the migration or travel time of magnetic particles 18*a* and 18*b* in glucose chamber 14 and reference chamber 16. In this way, sensor 12 or instrumentation 24 may determine, calculate, detect or sense the viscosity of the medium in glucose chamber 14. As mentioned above, the viscosity of the medium may be a function of, or dependent on concentration of glucose in the medium.

It should be noted that other sensing techniques may be employed to determine, measure or sense the proximity of magnetic particles 18*a* and 18*b*. Indeed, any and all techniques to determine the viscosity of the medium in glucose chamber 14, whether now known or later developed, are intended to be within the scope of the present invention.

In another aspect, the present invention is a system, device and technique that measures, detects calculates and/or senses the concentration of glucose in a fluid without breaking or physically penetrating the skin barrier. The detection techniques of this aspect of the invention may be optical, electrical, or mechanical in nature.

Figure 3:
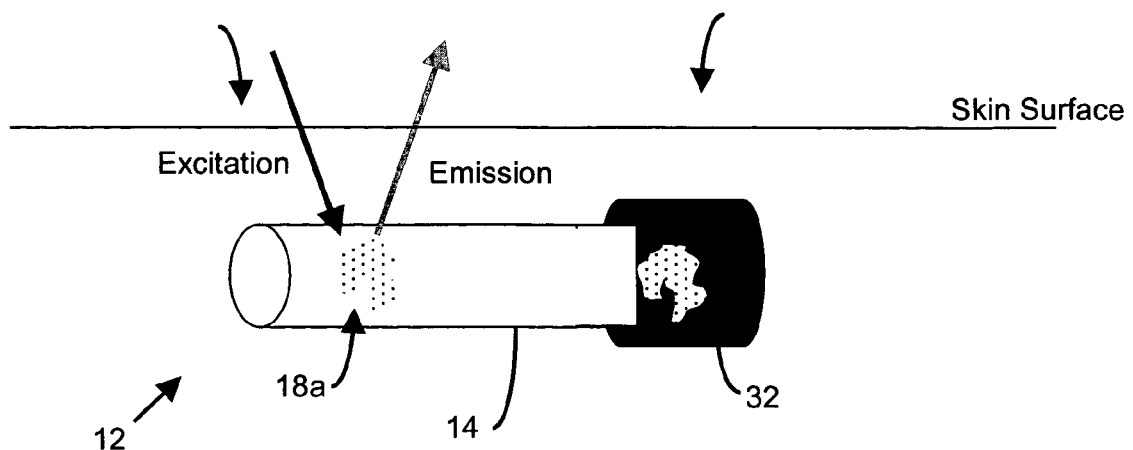
FIG. 3 is a schematic representation of a system, device and technique according to another embodiment of the present invention.

For example, with reference to FIG. 3, in one embodiment, the viscosity of the medium in glucose chamber 14 may be determined, calculated, detected or sensed using a optical technique that employs paramagnetic or superparamagnetic particles which are tagged with a fluorescent dye. In the illustrated embodiment, for simplicity, only glucose chamber 14 is depicted—although a reference chamber may also be implemented in the manner described above with respect to the embodiment illustrated in FIG. 2.

With continued reference to FIG. 3, sensor 12 may include glucose chamber 14 having magnetic particles 18*a* dispersed in a concanavalin A ("ConA")—dextran hydrocolloid fluid contained therein. As described above, when implanted, the glucose in the tissue surrounding glucose chamber 14 may enter glucose chamber 14 and effect, alter, modify or change the viscosity of the medium within chamber 14. As such, the viscosity of the medium within glucose chamber 14 may determine, effect, alter, modify or change the rate at which the magnetic particles 18*a* move, travel or migrate through glucose chamber 14 under the influence of an applied magnetic field.

In operation, a magnetic field is applied to induce or influence movement of particles 18*a* from position A to position B. As particles 18*a* move from point A towards position B, the fluorescent dye may be excited by fluorescence excitation light 34 that is disposed above sensor 12 and shone down on sensor 12 through the skin barrier of the animal body. The emission of the dye attached to particles 18*a* is measured, sensed, detected and/or recorded as particles 18*a* travel, move or migrate through glucose chamber 14. Once particles 18*a* arrive at position B, that is, under opaque cap 32, the fluorescence emission may no longer be measured or its strength may significantly decrease. This may be due to the fact that the dye attached to particles 18*a* is no longer accessible to fluorescence excitation light 34 or the fluorescence emission of the dye is blocked by opaque cap 32.

The time at which the particles reach the area under the cap may be determined by a decrease in fluorescence signal. The sensor 12 or instrumentation 24 may use the migration or travel time of the particles in glucose chamber 14 to determine, calculate or sense the viscosity of the medium in glucose chamber 14. As mentioned above, the viscosity of the medium may be a function of, or dependent on the concentration of glucose in the medium. As such, the migration or travel time of the particles in glucose chamber 14 may be used to determine or calculate the concentration of glucose in the medium in glucose chamber 14.

It should be noted that a converse arrangement wherein the majority of glucose chamber 14 may be opaque and a small transparent end may be employed to detect the arrival of the particles 18*a*. In this embodiment, a sudden appearance of a fluorescent signal indicates arrival of particles 18*a* at a location along glucose chamber 14. One or more of the above sensing modalities may be combined for a detection technique as well.

Figure 4:
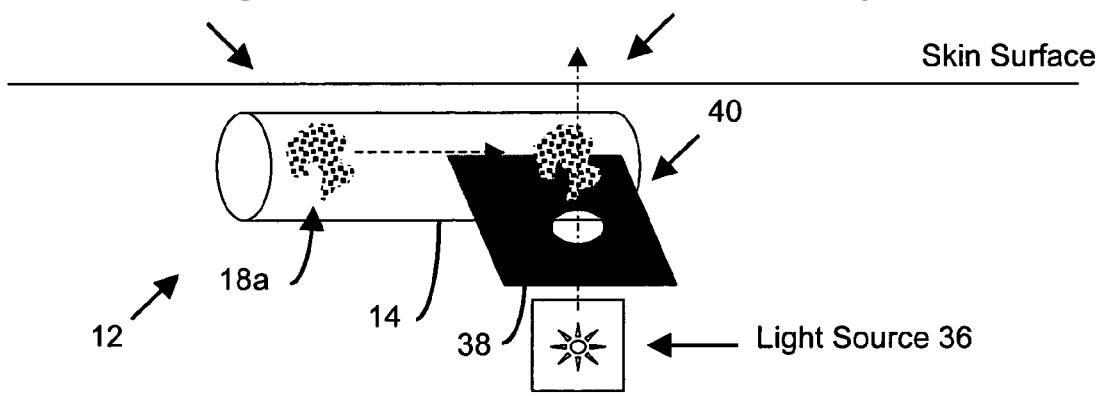
FIG. 4 is a schematic representation of a system, device and technique according to another embodiment of the present invention.

In another embodiment of this aspect of the present invention, an optical technique may be employed to detect or sense the position of particles 18*a* in chamber 14. With reference to FIG. 4, a light source 36 may be positioned and located beneath glucose chamber 14. The light source 36 may be partially obstructed by a mask 38 having an aperture 40 that is aligned with the interior of glucose chamber 14. Light or energy from light source 36 may be detected, measured and/or sensed by optical detector 42 (positioned above the skin surface) when the path of the light from source 36, through mask 38, and through glucose chamber 14 is unobstructed. When particles 18*a* move to a location above aperture 40 in mask 38, the energy from light source 36 is obstructed and the signal detected, measured and/or sensed by optical detector 42 weakens. The light source 36 may be powered by a self-contained battery (not depicted), or by energy inductively coupled through the skin to a receive coil (not illustrated) integrated with sensor 12 or light source 36. Other techniques may be employed to provide power to light source 36. Indeed, all techniques to provide power to light source 36, whether now known or later developed, are intended to be within the scope of the present invention.

Figure 5:
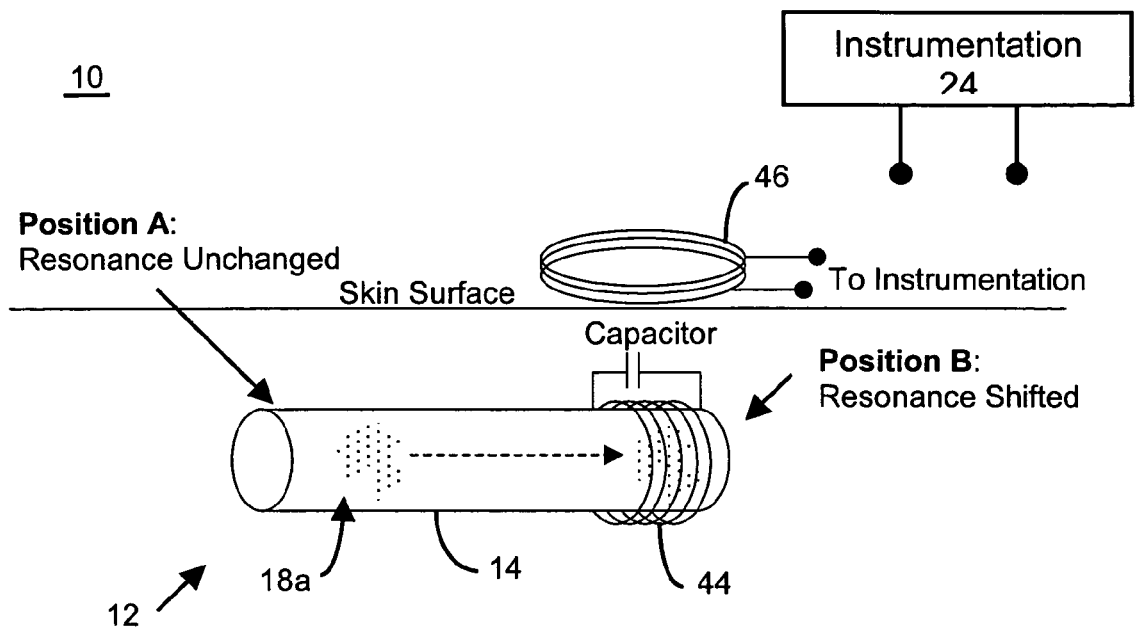
FIG. 5 is a schematic representation of a system, device and technique according to yet another embodiment of the present invention.

In another embodiment, a non-invasive electronic technique may be employed to determine, calculate and/or measure the concentration of glucose in the medium in glucose chamber 14. With reference to FIG. 5, in one embodiment, solenoid coil 44 may be disposed around one end of glucose chamber 14. Although not illustrated, a solenoid coil may also be disposed around reference chamber 16 as well. The solenoid coil 44 may be resonated to a particular radio frequency (RF) frequency with a capacitance or other circuitry well known to those skilled in the art.

In operation, when the core of solenoid coil 44 is filled with a material having a low relative electromagnetic permeability (i.e. the medium disposed within the core of coil 44 does not contain magnetic particles 18a), the resonance frequency of the coil, determined by the inductance and capacitance of the resonant circuit, is measured, established, and/or fixed at a first frequency. When magnetic particles 18a move, travel or migrate into the portion of chamber 14 including the core of solenoid 44, their higher relative electromagnetic permeability induces a shift in the inductance of solenoid 44 and hence a shift in the resonant frequency of the circuit (illustrated as coil 44 and a capacitor). The change in resonant frequency may be detected by, for example, "interrogating" solenoid 44 with an RF probe 46 located or positioned above the skin and coupled to appropriate instrumentation (for example, a spectrum analyzer).

It should be noted that other techniques may be employed to effect and/or detect a change in resonance. Indeed, all techniques to effect and/or detect that change, whether now known or later developed, are intended to be within the scope of the present invention.

In the embodiments described above, the particles 18a and 18b may be small spherical magnetic (paramagnetic or superparamagnetic) particles. Various other components or elements may be employed as a mobile component of sensor 12 and housed or contained within chambers 14 and 16. In this regard, particles 18a and 18b may be magnetic or non-magnetic. In those circumstances where non-magnetic particles are employed, the technique to effect or cause particle movement may be movement (rotation or translation) of sensor 12, mechanical force or thermal energy.

Further, the particles may have shapes other than spherical including but not limited to cylindrical, conical, ellipsoidal, or parallelepiped. Indeed, any shape may be employed and the particles in each chamber may be of a single shape or a mixture of shapes.

Moreover, the mobile component housed within the sensor may be made up of multiple particles or a single particle. As mentioned above, in those instances where paramagnetic, superparamagnetic, and/or ferromagnetic particles are employed, the particles may be may be any particle(s) which may be made or caused to move under the influence of a magnetic field or magnetomotive force, for example, rare earth elements like neodymium and samarium and compounds like neodymium-iron-boron and samarium-cobalt, and ferromagnetic materials including iron, permalloy, superpermalloy, cobalt, nickel, steel, and alnico. Indeed, any and all particles that may be caused to move under the influence of a magnetic field or magnetomotive force, whether now known or later developed, are intended to be within the scope of the present invention.

In the embodiments described above, the particles 18a and 18b move, travel or migrate from "side to side" within chambers 14 and 16. Other forms of particle movement may be employed. In this regard, the technique may be such that under normal conditions particles settle to the bottom of sensor 12. It is noted that the bottom of sensor 12 depends on sensor placement within the body and its resting relation with respect to the Earth's gravitational force. An external or an internal magnetic force may be employed to cause particles 18a and 18b to move towards the top of sensor 12 resulting in an up and down movement.

In one embodiment, the particles may remain in the same relative location and, under the influence of external or internal forces may be caused to rotate rather than translate within chambers 14 and 16. As such, the relative orientation of the particles may be employed (i.e., the particles include a means for differentiating either the top or bottom of a particle using, for example, various optical or mechanical properties of the particles), to determine whether the particle had rotated. Using that information, including the speed of rotation within sensor 12, the viscosity of the media in chambers 14 and 16 may be determined. As mentioned above, the viscosity of the media in chambers 14 and 16 may be may be employed to determine, calculate or measure the concentration of glucose in the medium in glucose chamber 14.

While the present invention has been described with reference to illustrative embodiments that include specific details, such embodiments and details should not be construed as limiting the scope of the invention. For example, as described above, embodiments of the present invention may employ particle movement techniques that do not include (partially or wholly) application of an external magnetic field to induce motion of paramagnetic, superparamagnetic, and/or ferromagnetic particles. In this regard, rather than an external permanent magnet, an electromagnet may be employed. The electromagnet may be incorporated into sensor 12.

Figure 6:
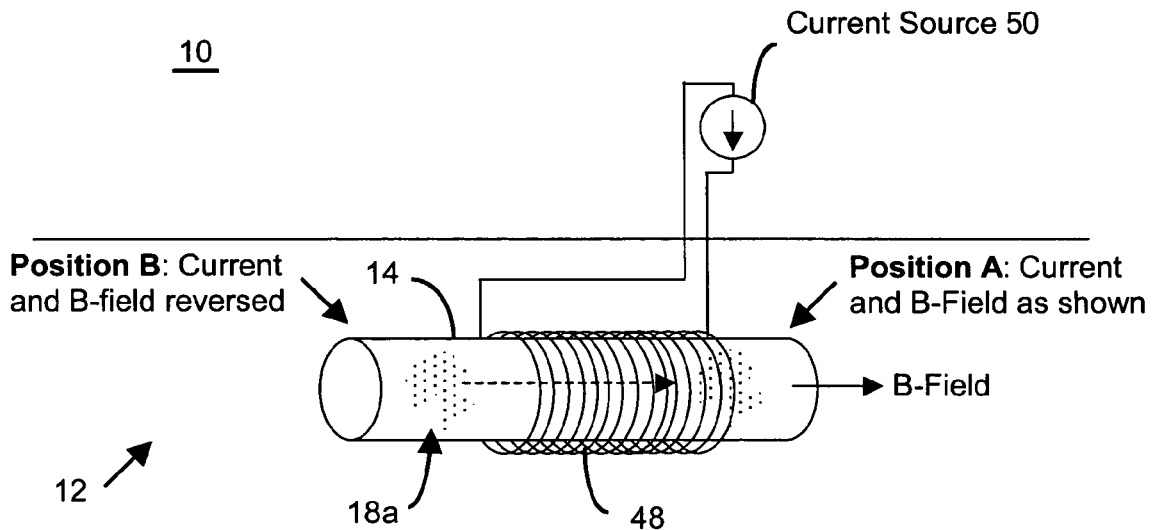
FIG. 6 is a schematic representation of a system, device and technique according to yet another embodiment of the present invention.

For example, with reference to FIG. 6, solenoid coil 48 may be used to generate a magnetic field that causes or drives the particles when a current is applied through solenoid 48. For simplicity, only one solenoid is illustrated. However, more than one solenoid coil may be employed to manipulate or cause the positions of the particles to move. Indeed, non-solenoid coil(s) may also be used.

The current source 50 is illustrated as being external to the body, connected by wires to (the indwelling or implanted) sensor 12. However, current source 50 may be supplied by an integrated power supply that is also implanted in the body, or may be generated by energy inductively coupled into sensor 12 using an outside coil and an implanted pick-up coil (as suggested above).

It should be noted that the sensor 12 may be placed in a location such as the earlobe or the webbing between the fingers such that a permanent magnet (or other applied force to cause movement of the particles) may be placed on alternate sides of sensor 12 when implanted in the body. In this embodiment, application of the magnetomotive force may be more efficient since the force may be more directly applied to the particles containing sensor 12.

In the preceding discussion, embodiments of the present invention have been described and illustrated with respect to implantation into the body of an animal for measurement of glucose in the fluids or body chambers within the animal. It should be appreciated that such embodiments as are described here may also be employed to measure glucose in fluids other than those inside the body of an animal, for example, in a cell culture reactor, or in commercial food or other processing systems where knowledge of glucose concentration is desirable. Notably, it is intended that the scope of the present invention extend to these uses of the sensor as well along with any adaptations required for its employment in these applications.

Moreover, in another aspect of the present invention, the sensor may include more than one glucose chamber and/or more than one reference chamber. These chambers may be located in the same general location or in different locations within the fluid, matrix or animal body. In this way, additional measurements may be obtained thereby providing a higher degree of confidence in the measured, sampled and/or sensed analyte concentration. It should be noted that the discussions of, for example, the solutions/fluids and magnetic particles, as well as the techniques for measuring, sampling and/or determining the concentration of glucose are fully applicable to this aspect of the present invention. Indeed, the entire discussion above with respect to the embodiments of FIGS. 1–6 is applicable to this multi-chamber embodiment. For the sake of brevity, those and all other discussions will not be repeated.

What is claimed is:

1. A glucose sensor for implantation within subcutaneous tissue of an animal body, the glucose sensor comprising:
    a first chamber containing (i) first magnetic particles and (ii) a first hydrocolloid solution having a viscosity which is dependent on and/or a function of the concentration of glucose in the first chamber, wherein the first magnetic particles are dispersed in the first hydrocolloid solution and wherein, when the first chamber is implanted in subcutaneous tissue of the animal body, glucose in the animal body may enter and exit the first chamber; and
    a reference chamber containing (i) second magnetic particles and (ii) a reference solution wherein the second magnetic particles are dispersed in the reference solution, and wherein, when the reference chamber is implanted in subcutaneous tissue of the animal body, glucose in the animal body does not enter the reference chamber.

2. The glucose sensor of claim 1 wherein the first hydrocolloid solution is a ConA-dextran hydrocolloid.

3. The glucose sensor of claim 2 wherein first hydrocolloid solution includes a combination of any glucose specific lectin, other glucose-specific binding protein, a glucose-containing glycoconjugate, or mannose-containing glycoconjugate.

4. The glucose sensor of claim 1 wherein the reference solution is a second hydrocolloid solution.

5. The glucose sensor of claim 4 wherein the second hydrocolloid solution is a ConA-dextran hydrocolloid.

6. The glucose sensor of claim 5 wherein second hydrocolloid solution includes a combination of any glucose specific lectin, other glucose-specific binding protein, a glucose-containing glycoconjugate, or mannose-containing glycoconjugate.

7. The glucose sensor of claim 1 wherein the first and second magnetic particles are amine-terminated particles.

8. The glucose sensor of claim 7 wherein the amine-terminated particles having a mean diameter of about 1 µm.

9. The glucose sensor of claim 1 wherein the first and second magnetic particles include at least one rare earth element.

10. The glucose sensor of claim 9 wherein the at least one rare earth element is selected from the group consisting of neodymium and samarium.

11. The glucose sensor of claim 1 wherein the first and second magnetic particles are selected from the group consisting of neodymium, samarium, neodymium-iron-boron, samarium-cobalt, iron, permalloy, superpermalloy, cobalt, nickel, steel, and alnico.

12. The glucose sensor of claim 1 wherein the first and second magnetic particles include a ferromagnetic material.

13. The glucose sensor of claim 1 wherein the first chamber includes a semipermeable membrane.

14. The glucose sensor of claim 1 wherein the first chamber includes a semipermeable membrane comprising regenerated cellulose, polyurethane, polysulfone or other material that is capable of unrestricted glucose in and efflux.

15. The glucose sensor of claim 1 wherein the first chamber is a dialysis hollow fiber having semipermeable membrane properties.

16. A glucose sensing system comprising:
    a glucose sensor which is implanted in subcutaneous tissue of an animal body, the glucose sensor including:
        a first chamber containing (i) first magnetic particles and (ii) a hydrocolloid solution having a viscosity which is dependent on and/or a function of the concentration of glucose in the first chamber, wherein the first magnetic particles are dispersed in the hydrocolloid solution and wherein, when the first chamber is implanted in subcutaneous tissue of an animal body, glucose in the animal body may enter and exit the first chamber; and
        a reference chamber containing (i) second magnetic particles and (ii) a reference solution wherein the second magnetic particles are dispersed in the reference solution; and
    instrumentation to determine data which is representative of a change in viscosity of the hydrocolloid solution in the first chamber.

17. The glucose sensing system of claim 16 wherein the hydrocolloid solution includes a known viscosity.

18. The glucose sensing system of claim 16 wherein the reference solution includes a constant viscosity.

19. The glucose sensing system of claim 16 wherein the reference solution includes a known viscosity.

20. The glucose sensing system of claim 16 wherein the reference solution includes oil or alcohol compounds.

21. The glucose sensing system of claim 16 wherein the hydrocolloid solution is a ConA-dextran hydrocolloid.

22. The glucose sensing system of claim 16 wherein the hydrocolloid solution includes any glucose specific lectin, other glucose-specific binding protein, a glucose-containing glycoconjugate, or mannose-containing glycoconjugate.

23. The glucose sensing system of claim 16 wherein the first magnetic particles are amine-terminated particles.

24. The glucose sensing system of claim 23 wherein the amine-terminated particles having a mean diameter of about 1 µm.

25. The glucose sensing system of claim 16 wherein the first magnetic particles include at least one rare earth element.

26. The glucose sensing system of claim 16 wherein the first magnetic particles include a ferromagnetic material.

27. The glucose sensing system of claim 16 wherein the first chamber includes a semipermeable membrane.

28. The glucose sensing system of claim 16 wherein the first chamber includes a semipermeable membrane comprising regenerated cellulose, polyurethane, polysulfone or other material that is capable of unrestricted glucose in and efflux.

29. The glucose sensing system of claim 16 wherein the first chamber is a dialysis hollow fiber having semipermeable membrane properties.

30. A glucose sensor for measuring the concentration of glucose in a fluid medium, the glucose sensing comprising:
a first chamber containing (i) first magnetic particles and (ii) a hydrocolloid solution having a viscosity which is dependent on and/or a function of the concentration of glucose in the first chamber, wherein the first magnetic particles are dispersed in the hydrocolloid solution and wherein, when the first chamber is in fluidic contact with the fluid medium, glucose from the fluid medium may enter and exit the first chamber; and
a reference chamber containing (i) second magnetic particles and (ii) a reference solution wherein the second magnetic particles are dispersed in the reference solution, and wherein, when the reference chamber is in fluidic contact with the fluid medium, glucose from the fluid medium does not enter the reference chamber.

31. The glucose sensor of claim 30 wherein the hydrocolloid solution includes a known viscosity.

32. The glucose sensor of claim 30 wherein the reference solution includes a constant viscosity.

33. The glucose sensor of claim 30 wherein the reference solution includes a known viscosity.

34. The glucose sensor of claim 30 wherein the reference solution includes oil or alcohol compounds.

35. The glucose sensor of claim 30 wherein the hydrocolloid solution is a ConA-dextran hydrocolloid.

36. The glucose sensor of claim 30 wherein the hydrocolloid solution includes any glucose specific lectin, other glucose-specific binding protein, a glucose-containing glycoconjugate, or mannose-containing glycoconjugate.

37. The glucose sensor of claim 30 wherein the first magnetic particles are amine-terminated particles.

38. The glucose sensor of claim 37 wherein the amine-terminated particles having a mean diameter of about 1 µm.

39. The glucose sensor of claim 30 wherein the first magnetic particles include at least one rare earth element.

40. The glucose sensor of claim 30 wherein the first magnetic particles include a ferromagnetic material.

41. The glucose sensor of claim 30 wherein the first chamber includes a semipermeable membrane.

42. The glucose sensor of claim 30 wherein the first and second magnetic particles include at least one rare earth element.

43. The glucose sensor of claim 42 wherein the at least one rare earth element is selected from the group consisting of neodymium and samarium.

44. The glucose sensor of claim 30 wherein the first and second magnetic particles are selected from the group consisting of neodymium, samarium, neodymium-iron-boron, samarium-cobalt, iron, permalloy, superpermalloy, cobalt, nickel, steel, and alnico.

45. The glucose sensor of claim 30 wherein the first and second magnetic particles include a ferromagnetic material.

46. The glucose sensor of claim 30 wherein the viscosity of the first hydrocolloid solution changes in response to the presence of glucose.

47. The glucose sensor of claim 30 wherein the first chamber includes a semipermeable membrane comprising regenerated cellulose, polyurethane, polysulfone, or other material that is capable of unrestricted glucose in and efflux.

48. The glucose sensor of claim 30 wherein the first chamber is a dialysis hollow fiber having semipermeable membrane properties.

49. A glucose sensor for measuring the concentration of glucose in a fluid, the glucose sensing comprising:
a first chamber;
a first plurality of magnetic particles disposed in the first chamber;
a first solution disposed in the first chamber, wherein the first solution includes a viscosity which is dependent on and/or a function of the concentration of glucose in the first chamber; and
wherein the first plurality of magnetic particles are dispersed in the first solution and wherein, when the first chamber is in fluidic contact with the fluid, glucose in the fluid may enter and exit the first chamber.

50. The glucose sensor of claim 49 wherein the first solution includes a hydrocolloid.

51. The glucose sensor of claim 50 wherein the hydrocolloid is a solution of glucose-binding molecules and macromolecules.

52. The glucose sensor of claim 51 wherein the macromolecules are glucose-terminated or mannose-terminated.

53. The glucose sensor of claim 51 wherein the glucose binding molecules are Concanavalin A and the macromolecules are dextran.

54. The glucose sensor sensing of claim 51 wherein the device further includes a semipermeable membrane wherein the first chamber is enclosed by the semipermeable membrane.

55. The glucose sensor of claim 54 wherein the semipermeable membrane is a hollow cellulose acetate dialysis fiber.

56. The glucose sensor of claim 51 further including:
a second chamber, wherein the second chamber includes a second solution and a second plurality of magnetic particles; and
wherein the second plurality of magnetic particles are dispersed in the second solution.

57. The glucose sensor of claim 56 wherein second solution is a hydrocolloid, an oil, or an alcohol.

58. The glucose sensor of claim 56 further including an impermeable membrane wherein the second chamber is enclosed by the impermeable membrane.

59. The glucose sensor of claim 49 wherein the first plurality of magnetic particles are capable of moving within the first solution.

60. The glucose sensor of claim 1 wherein the hydrocolloid solution includes a known viscosity and the reference solution includes a constant viscosity.

61. The glucose sensor of claim 1 wherein the hydrocolloid solution includes a known viscosity and the reference solution includes a known viscosity.

62. The glucose sensor of claim 1 wherein the reference solution includes oil or alcohol compounds.

63. The glucose sensor of claim 1 wherein the first magnetic particles are amine-terminated particles.

64. The glucose sensor of claim 63 wherein the amine-terminated particles having a mean diameter of about 1 µm.

65. The glucose sensor of claim 1 wherein the first magnetic particles include at least one rare earth element.

66. The glucose sensor of claim 1 wherein the first magnetic particles include a ferromagnetic material.

* * * * *